United States Patent
Ricke et al.

(10) Patent No.: US 7,783,341 B2
(45) Date of Patent: Aug. 24, 2010

(54) METHOD AND APPARATUS FOR DISCERNING THERAPEUTIC SIGNALS FROM NOISE IN PHYSIOLOGICAL DATA

(75) Inventors: Anthony Ricke, Wauwatosa, WI (US); Gordon Ian Rowlandson, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 424 days.

(21) Appl. No.: 11/970,277

(22) Filed: Jan. 7, 2008

(65) Prior Publication Data
US 2009/0177106 A1 Jul. 9, 2009

(51) Int. Cl.
*A61B 5/04* (2006.01)
(52) U.S. Cl. ...................................... 600/523
(58) Field of Classification Search ................. 600/509, 600/510, 523
See application file for complete search history.

(56) References Cited

U.S. PATENT DOCUMENTS

| | | | |
|---|---|---|---|
| 5,448,997 A * | 9/1995 | Kruse et al. ................ | 600/510 |
| 6,304,772 B1 | 10/2001 | Taha et al. | |
| 6,477,404 B1 | 11/2002 | Yonce et al. | |
| 2004/0267146 A1 | 12/2004 | Yonce | |
| 2005/0220907 A1 | 10/2005 | Theoharides | |
| 2006/0020219 A1 | 1/2006 | Zinser, Jr. et al. | |
| 2006/0069321 A1 | 3/2006 | Zinser, Jr. et al. | |

OTHER PUBLICATIONS

Abildskov, J.A. et al; The Relation of Precordial and Orthogonal Leads; Journal of the American Heart Association; Jan. 1963; vol. XXVII, pp. 58-63.

* cited by examiner

*Primary Examiner*—Carl H Layno
*Assistant Examiner*—Brian T Gedeon
(74) *Attorney, Agent, or Firm*—Andrus, Sceales, Starke & Sawall, LLP (57) ABSTRACT

A data acquisition module for use in monitoring a plurality of physiological signals is disclosed herein. The data acquisition module may include a first signal processing path for biopotential data, a second signal processing path for therapeutic event data, and a processing unit that receives and processes the data from the first and second signal processing paths. The data acquisition module may further compare identified likely therapeutic events in each of a plurality of psychological signals. A method of identifying an electronic therapeutic event from a physiological signal is also disclosed herein the method may include steps of obtaining a plurality of psychological signals, removing any biopotential data from the physiological signals, using a first technique to identify likely therapeutic event data, comparing the identified likely therapeutic event data from each of the plurality of physiological signals and refining the identification of likely therapeutic events based on the comparison between each of the plurality of physiological signals.

14 Claims, 6 Drawing Sheets

METHOD AND APPARATUS FOR DISCERNING THERAPEUTIC SIGNALS FROM NOISE IN PHYSIOLOGICAL DATA

FIELD OF THE DISCLOSURE

The present disclosure relates generally to the field of monitoring physiological data obtained from a patient. More specifically, the present disclosure relates to the detection of therapeutic artifacts from implanted medical devices.

BACKGROUND

Electrical impulses originating in the tissues of the heart cause the heart to cyclically contract. When, due to heart disease or tissue damage, the heart tissue fails to properly create and/or propagate these electrical impulses, an artificial electronic pace maker may be implanted to provide the necessary simulation.

Clinicians must be made aware of patients that have been treated with an implantable pacemaker due to the adverse effects that may result from the provision of certain drugs and/or medical procedures unknowingly upon a patient who has an implanted pacemaker. However, the clinician is not always made aware of the existence of an implanted pace maker within the patient, nor are pacemaker electrical pulses readily discernable when viewing a patient's electrocardiograph (ECG). Therefore, certain medical standards require that ECG monitoring and analysis systems include electronic pace maker pulse identification algorithms and labeling.

The detection of pacing stimulus artifacts from implanted electronic pace makers is sometimes difficult due the present use of sophisticated pacemaker pulse generation algorithms and low-energy output waveforms for stimulating the heart muscle. In addition, improvements in ECG collection and processing technology have reduced the noise artifacts that exist in the collected ECG signal. While this has improved ECG signal quality, it has made it harder to detect artificially generated stimulation.

The detection of electronic pacemaker pulse artifacts in an ECG signal is further complicated by the signal characteristics of the pacemaker pulses and the ECG signals themselves. The bandwidth of a normal ECG signal is generally between 0.5 and 150 Hz, with advanced applications of the ECG reaching a maximum of 300 HZ. On the other hand, the bandwidth of the pacemaker pulse signals is generally between 250 Hz and 10 kHz. Therefore, there is very little noise generated by artificial stimulation of the heart that corrupts the ECG signal outside of 60 Hz line frequency noise.

Although it is relatively easy to isolate and enhance the physiological signal for the purposes of ECG analysis, it is more complicated to acquire both the physiological signal and the pacemaker pulse signals for the optimum assessment of each. This is because the large bandwidth of the pace maker pulse signals (250 Hz to 10 KHz) overlaps with the frequency content of other noise generated by man-made electrical sources or static. These other noise sources can be very large and intermittent. As a result, they can corrupt or saturate the digital acquisition of the low-frequency physiological signal. Furthermore, the signal-to-noise characteristics of the acquisition hardware required for the physiological signal is much higher than the signal-to-noise characteristics for the pacemaker signals. As a result, a dual path for each type of signal is warranted.

BRIEF DISCLOSURE

In the field of patient physiological data monitoring and physiological data processing, embodiments of a method of identifying an electronic therapeutic event from a physiological signal are disclosed herein. Embodiments of the method may include obtaining a plurality of physiological signals from a plurality of electrodes. The obtained physiological signals may comprise biopotential data, therapeutic event data, and/or noise. Embodiments of the method may further comprise removing the biopotential data from the physiological data, using a first technique to identify likely therapeutic event data, comparing the identified likely therapeutic event data from each of the plurality of physiological signals, and refining the identification of therapeutic events based upon the comparison of each of the plurality of physiological signals.

Additionally, a data acquisition module for use in obtaining a plurality of physiological signals comprising biopotential data and therapeutic event data is disclosed herein. Embodiments of the module may include a first signal processing path for isolating and enhancing the biopotential data of the plurality of physiological signals and a second signal processing path for identifying therapeutic event data from the plurality of physiological signals. Embodiments of the data acquisition module may further include a processing unit that receives and processes the biopotential data from the first signal processing path and the therapeutic event data from the second signal processing path. A signal processing module may be associated with the processing unit and the signal processing module may receive the therapeutic event data and apply a first signal processing technique to identify likely therapeutic events. Embodiments of the data acquisition module may also include a precordial sweep module that compares the identified likely therapeutic events from each of the plurality of physiological signals and a pace pulse determination module.

Herein disclosed are still further embodiments of a computer readable medium configured with computer readable code. The computer readable medium may be configured such that the execution of the computer readable code has the effect of receiving a plurality of physiological signals comprising at least one biopotential signal and at least one therapeutic event signal, isolating the biopotential signals from the therapeutic event signals, measuring the signal characteristics of the therapeutic event signals to identify potential therapeutic events, comparing the potential therapeutic events identified in each of the therapeutic event signals, and determining the validity of potential therapeutic events. Still further embodiments of the computer readable medium may further be configured such as to, upon execution, have the effect of: computing a first qualification confidence interval based on the measured signal characteristics, and computing a second qualification confidence interval based on the comparison of the potential therapeutic events.

DETAILED DISCLOSURE

Figure 1:
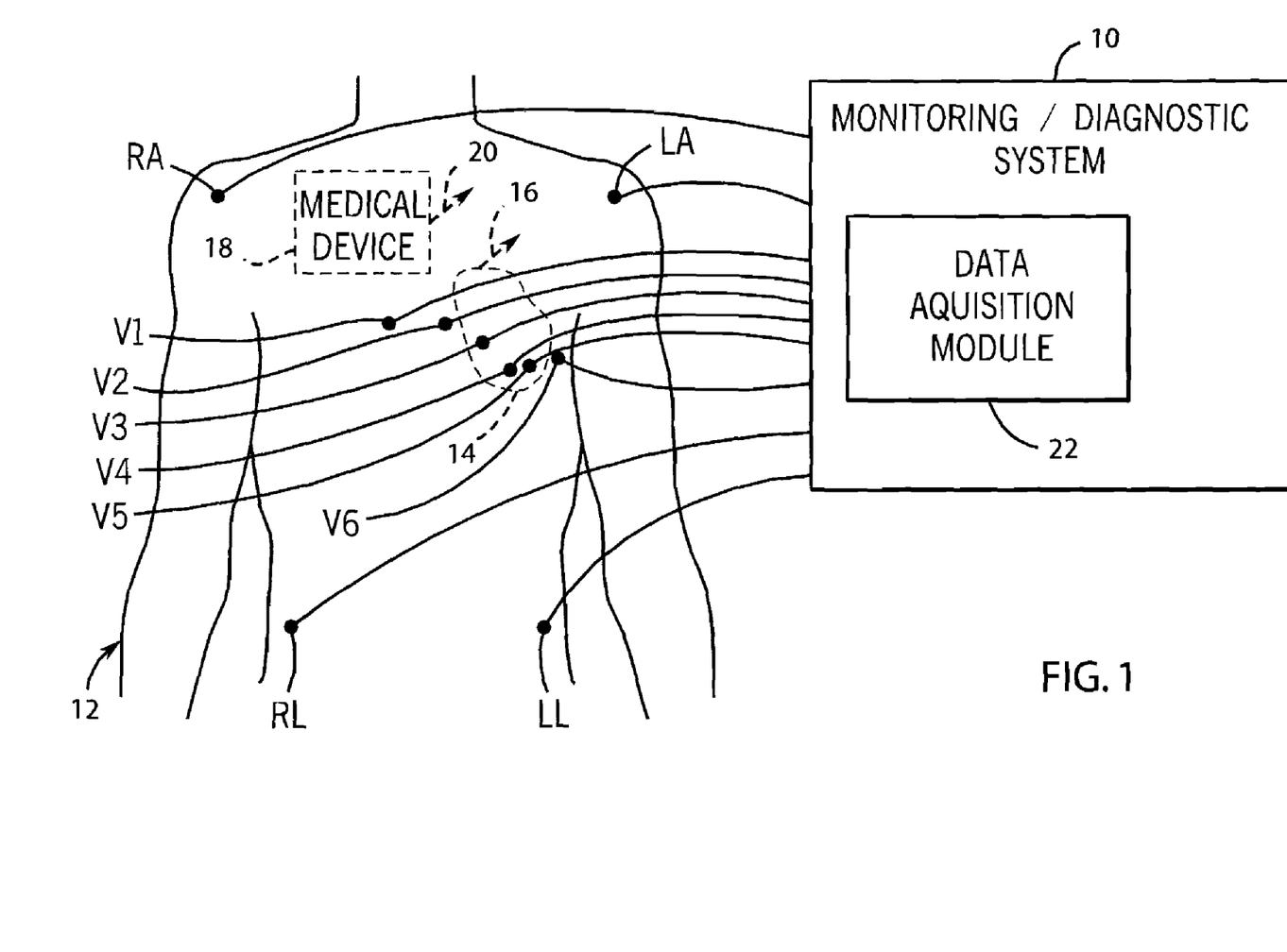
FIG. 1 depicts an embodiment of a diagnostic monitoring system connected to an electrode configuration suitable to collect a standard twelve-lead electrocardiograph.

FIG. 1 depicts a monitoring system 10 that is connected to a patient 12. In alternative embodiments, the monitoring system 10 may also be diagnostic system that aids the clinician in interpreting the physiological data. The monitoring system 10 is connected to the patient 12 via a plurality of electrodes (labeled RA, LA, RL, LL, V1, V2, V3, V4, V5 and V6). The electrodes are typically placed at standard anatomical locations as in accordance with the standard acquisition of a twelve-lead electrocardiogram (ECG). A twelve-lead ECG utilizes four limb electrodes (RA, LA, RL, LL) and six precordial electrodes (V1, V2, V3, V4, V5, and V6). Differential voltages are obtained between two or more of these electrodes to obtain leads or slices through the heart along which the electrical characteristics of the heart are measured.

The heart 14 of the patient 12 produces an electrical impulse 16 at regular intervals. The electrical impulse causes the muscle tissue of the heart to contract as the electrical impulse 16 propagates through the heart. The resulting electrical potential generated at the patient's skin due to the propagation of this electrical impulse through the heart muscle tissue is measured by each of the electrodes and represented by each of the ECG leads.

Often, when the heart tissue is damaged or diseased the heart improperly generates or propagates the electrical impulses and fails to properly contract. In this situation, an implantable medical device 18, such as a pace maker or defibrillator, is placed inside the body of the patient 12. The implantable medical device 18 generates its own electrical impulses 20 to stimulate the tissue of the heart 14 such that the heart 14 properly contracts.

The electrodes placed on the patient 12 are merely electrical transducers, and as such pick up all electrical energy at the electrode location and provide the sensed electrical signals to the data acquisition module 22 of the monitoring system 10. Therefore, the data acquisition module 22 acquires not only the electrical heart impulses 16, but the implantable medical device impulses 20 as well as electrical noise from any number of sources in and around the patient. The electrical noise may include electromagnetic noise from man-made sources, electrical impulses from other medical devices used to provide care to the patient, and from other biopotentials generated by the patient such as muscle contractions (EMG) and/or brain waves (EEG).

Figure 2:
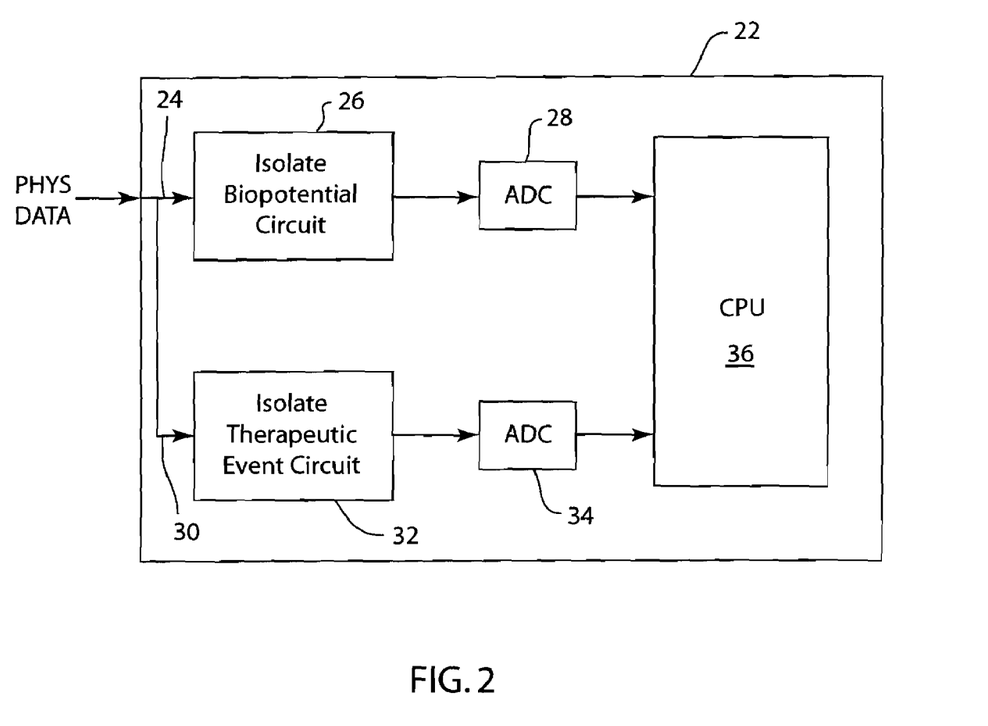
FIG. 2 depicts an embodiment of a data acquisition module.

FIG. 2 depicts a more detailed embodiment of the data acquisition module 22. The data acquisition module 22 receives the physiological data from the electrodes and processes the physiological data along two data processing paths. The first data processing path 24 serves to isolate and process the ECG component of the raw physiological data. This biopotential data is typically most important and/or clinically relevant data obtained in such a system. The biopotential data (in this case ECG data) provides the most information regarding the patient's physiological condition and bodily function. The ECG data may be isolated from the physiological data by an isolation biopotential circuit 26. As stated above, the frequency content of the ECG signal is typically between 0.5 Hz and 150 Hz, therefore, the isolation biopotential circuit 26 may include a low pass filter. Next, the isolated ECG signal may be digitized using an analog-to-digital converter (ADC) 28. An exemplary sampling frequency for an ECG signal may be 2 kHz; however, this is not intended to be limiting on the frequencies at which the ECG may be sampled. Finally, the digitized ECG signal from the first data processing path 24 may be provided to a controller or CPU 28 for further data processing as explained herein.

The physiological data is also processed by the data acquisition module 22 along a second data processing path 30. The purpose of the second data processing path is to isolate and enhance the therapeutic event signal that, in the embodiment described herein, is provided by the implantable medical device 18. This may be achieved by an isolation therapeutic event circuit 32. As explained above, the bandwidth of the therapeutic event signal may be much greater than that of the previously described ECG signal. Therefore, the isolation therapeutic event circuit 32 may comprise a bandpass filter with a pass band between 250 Hz and 15 kHz; however, the aforementioned pass band is merely exemplary and is not intended to be limiting on the types of filtering or pass band that may be implemented in embodiments of the solution therapeutic event circuit 32.

Next, the filtered therapeutic event signal may be digitized by ADC 34. As the therapeutic event signal may have a greater frequency content than the ECG signal, ADC 34 may sample at a much higher frequency than ADC 28. Since an exemplary sampling rate, the ADC 34 may sample at a rate of 75 kHz; however, this sampling rate is not intended to be limiting on the range of sampling rates that may be used by ADC 34. Finally, the digitized therapeutic event signal is provided to CPU 28 for further processing as disclosed herein.

In an alternative embodiment of the data acquisition module 22, a single multiplexer (not depicted) may be utilized to sample each of the electrodes such that multiple sets of data processing paths are not needed. In embodiments not using a multiplexer, a first 24 and second 30 data processing path may be needed for each physiological data lead. The use of a multiplexor may reduce implementation and component costs by eliminating the redundancy that would be required to process all of the physiological data simultaneously.

Figure 3:
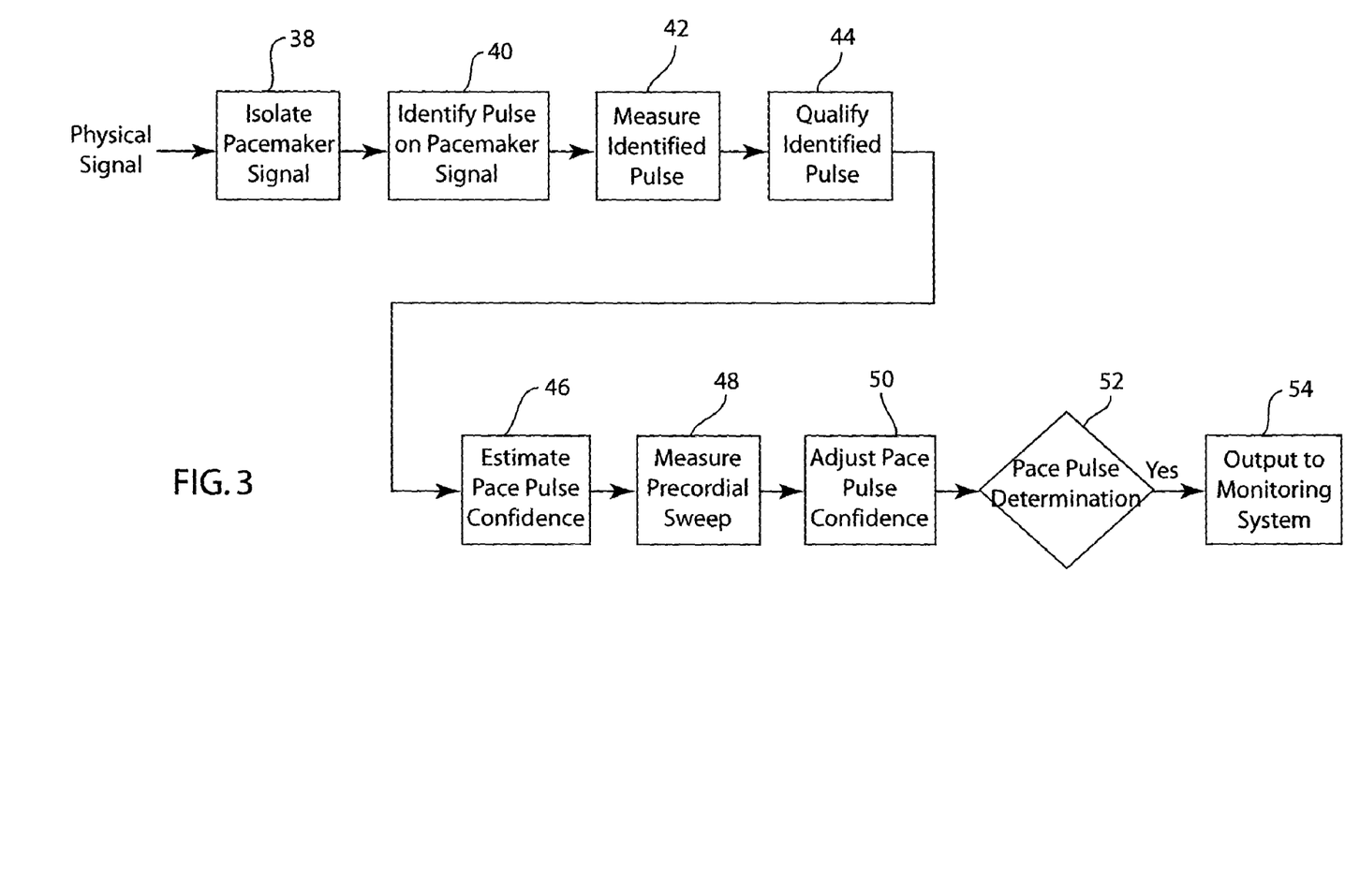
FIG. 3 is a flow chart of an embodiment of a method carried out by the data acquisition module.
Figure 4A:
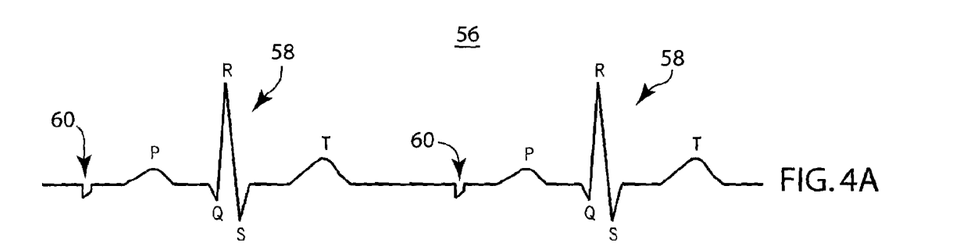
FIG. 4 depicts electrocardiographs of the six precordial leads.
Figure 4B:
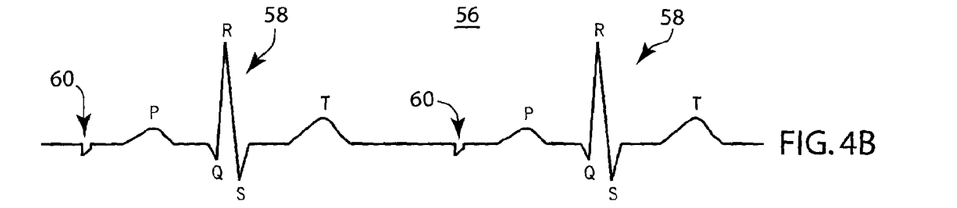
Figure 4C:
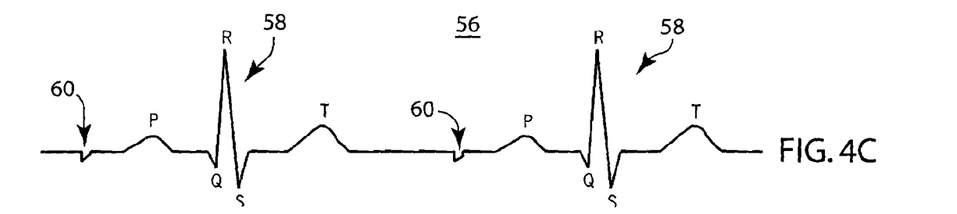
Figure 4D:
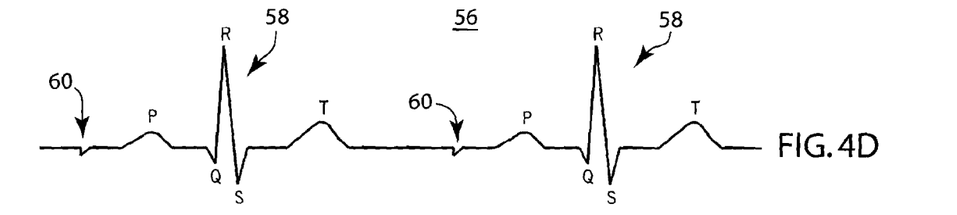
Figure 4E:
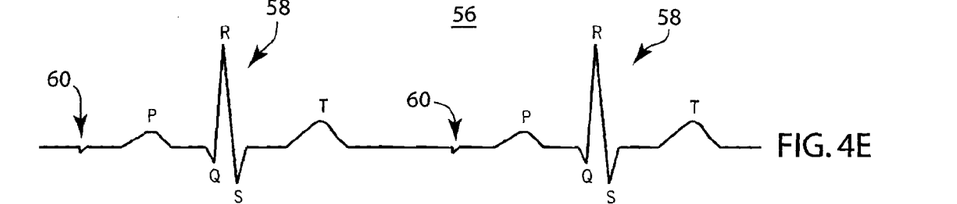
Figure 4F:
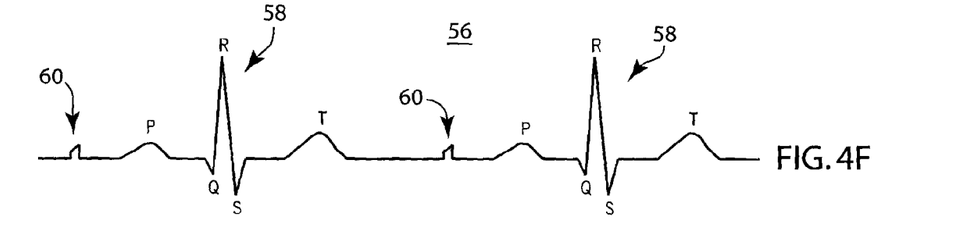

FIG. 3 is a flow chart depicting an embodiment for a method of processing a physiological signal to identify therapeutic events such as pacemaker signals. The embodiment of the method as depicted in FIG. 3 is exemplarily disclosed in processing an ECG physiological signal to identify pacemaker pulses; however, it is understood that embodiments of the method disclosed herein may be applied to the monitoring and/or interpretation of other biopotential signals. First, at step 38, the pacemaker signal is isolated from the collected physiological signal. As described above, in some embodiments, this may be implemented through the use of a band pass filter. Next, likely pacemaker pulses from the isolated pacemaker signal are identified in step 40. The likely pacemaker pulses may be identified as those pulses that match certain predetermined threshold criteria for signal characteristics such as amplitude, pulse width, slew rate, and/or pulse energy. In step 42 pulse amplitude, pulse width and/or other signal characteristics are measured and may be recorded for each of the identified likely pacemaker pulses. While steps 40 and 42 have been depicted in this flow chart in a particular order, it is understood that these steps may be performed in reverse order or simultaneously within the scope of the disclosed method as the order of these steps may be determined by the implementation of the method or other related considerations.

After the identified likely pace maker pulses have been identified and measured, these likely pulses may be qualified at step 44. In qualifying the pace maker pulses, the pace maker pulses may be compared to the ECG signal obtained from the physiological signal such as to identify the likely pace maker pulses that occur at the proper timing with the ECG signal as would be expected for a pacemaker pulse. Alternatively, the likely pacemaker pulses may be qualified at step 44 by selecting those pulses that meet certain predetermined criteria of pulse measurements taken in step 42. In an alternative embodiment, the likely pacemaker pulses may be qualified in step 44 by pulse matching, or by the comparison of the identified likely pacemaker pulses to stored standardized or archetypal of pacemaker pulse waveforms. In a still further embodiment, step 44 is bypassed and all identified likely pacemaker pulses are passed on as qualified.

Next, at step 46, a confidence interval is estimated for each of the identified pacemaker pulses. The estimation of the confidence interval for the likely pacemaker pulses may be stored on a data storage device (not depicted) such that the estimated confidence intervals for each of the pacemaker pulses may be referenced at later steps, as disclosed herein.

Next, at step 48, the isolated pacemaker signals for each of the acquired ECG leads are compared to each other to measure the precordial sweep. The number of ECG leads that are compared may include the six standard precordial leads, but may also use the precordial leads from a reduced precordial lead set, such as one that is comprised of fewer than six precordial leads. Alternatively, the precordial leads may include those leads of an expanded lead set such as to include one or more of the leads labeled V4R, V5R, V6R, V7, V8, and V9.

Figure 5:
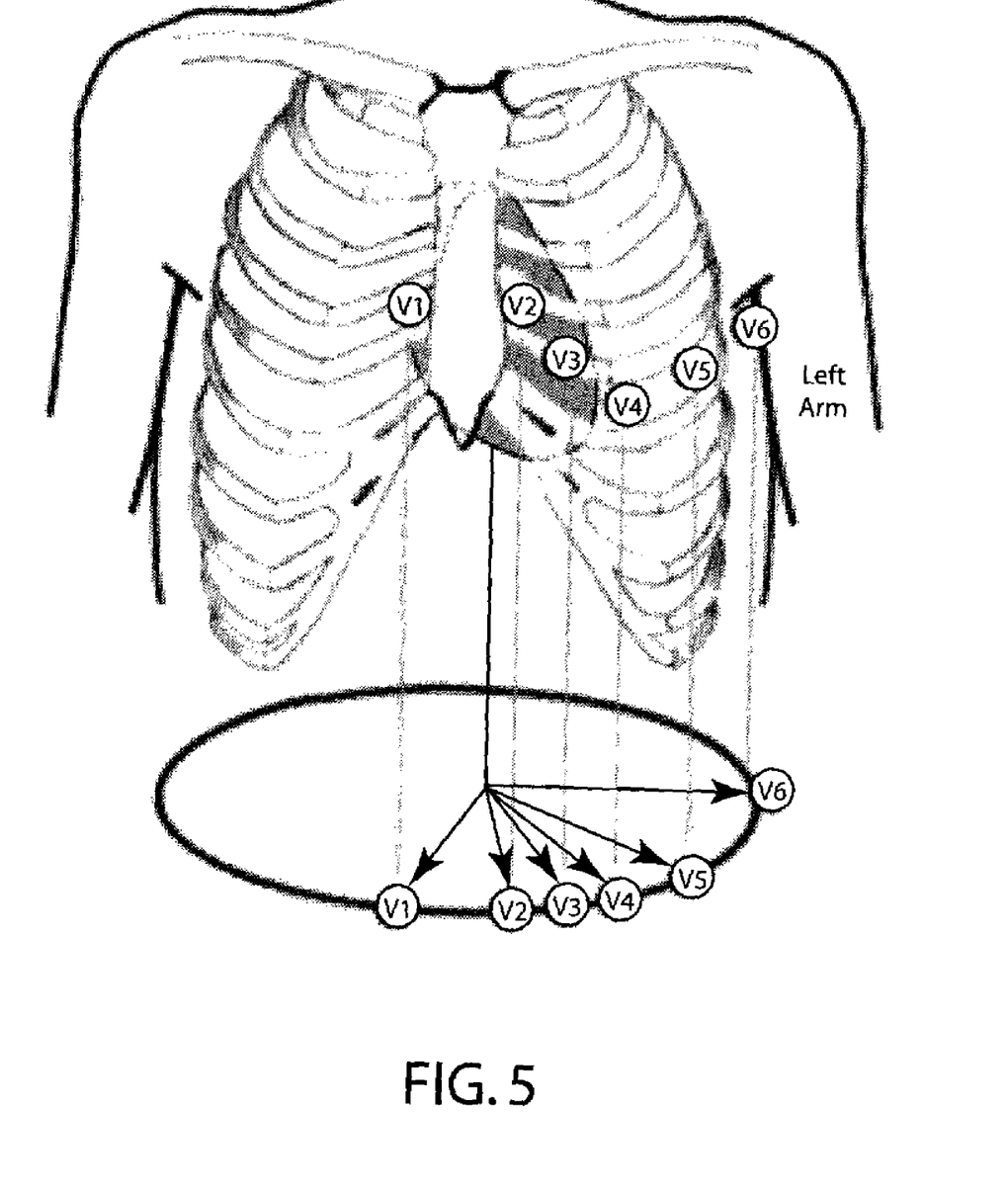
FIG. 5 depicts the orientation and proper placement of the six precordial leads on the patient.

Referring to FIGS. 4 and 5, FIG. 4 depicts exemplary ECG traces 56 for each of the V1-V6 leads. Each ECG trace 56 includes a series of ECG complexes 58 and a series of pacemaker pulses 60. Common features of the ECG complexes 58 include the P-wave, the QRS complex and the T-wave. Often the pacemaker pulses 60 are characterized by a trapezoidal shape, as depicted in FIG. 4; however, this need not be the case as advanced pacemaker pulse control algorithm may create pacemaker pulses of alternative waveforms. Since the pacemaker pulse is an electrical impulse that travels through the body, the pacemaker pulse may be represented by a three-dimensional vector having its source at the pacemaker.

In the step of measuring precordial sweep 48, the pacemaker pulses 60 are compared between each of the recorded precordial leads 56. Referring to FIG. 5, the placement of the precordial electrodes upon the chest of the patient is depicted along with the resulting angles that are formed between each electrode and the pacemaker pulse vector. Therefore, as can be seen with respect to FIGS. 4 and 5, an electrical impulse that has its source internal to the patient such as a cardiac impulse or a pacemaker pulse, the electrical impulse will occur at a slightly different angle to each of the precordial leads. This can be seen in FIG. 4 by comparing the pacemaker pulses 60 between each of the precordial lead traces 56. This phenomenon is referred to in the present disclosure as precordial sweep.

Precordial sweep is characterized by a gradual change in the amplitude of the measured pacemaker pulse measured between precordial leads. This change occurs due to the alignment of the pacemaker pulse vector and the precordial leads. As can be seen by reference to FIGS. 4 and 5, the precordial electrodes V1 and V6 are more than 90° apart (typically 115°). Therefore, the polarity of the pacemaker pulse measured at V1 is typically opposite that of the pacemaker pulse detected at V6. It may be further noted that in the typical precordial sweep, the amplitude of the pacemaker pulse 60 gradually decreases until the angle between the precordial electrode and the pacemaker pulse vector is greater than 90°. At this point, the polarity of the detected pacemaker pulse reverses and the detected pacemaker pulse amplitude begins to increase.

The step of measuring the precordial sweep may be performed by comparing the recorded precordial leads to look for the aforementioned characteristic precordial sweep between the measured precordial leads. Additionally, the step of measuring the precordial sweep may also look to the polarities of the pacemaker pulses detected at the V1 and V6 electrodes. An opposite polarity of the pacemaker pulses at the V1 and V6 electrode may generally be indicative of the identified likely pacemaker pulse being a true pacemaker pulse. Another, more basic, measurement may be the detection of the presence of the likely pacemaker pulse in each of the measured precordial leads.

The step of measuring the precordial sweep aids in the determination of true pacemaker pulses based upon the physiology of the pacemaker pulses. The pacemaker pulse is generated internally since the pacemaker device is implanted in the patient's body and the pacemaker electrodes are connected to the heart of the patient. The pacemaker pulse is in the form of a vector and therefore has a magnitude and a three-dimensional direction. Each precordial lead records this vector at a different angle from the pacemaker pulse generation site (the heart). That is, the pacemaker pulse vector is projected onto an imaginary plane at each precordial lead where the imaginary plane is tangent to the surface of the skin at the lead. The result of this is that the precordial lead that is the closest in direction to the pacemaker pulse vector will depict the pace maker pulse vector with the maximum amplitude. As the precordial leads form greater and greater angles with the generated pacemaker pulse vector, the recorded pacemaker pulse in each of the precordial leads is reduced until a precordial lead that is perpendicular to the pacemaker pulse vector, will depict little or no pacemaker pulse. Precordial leads that are at an angle greater than 90° to the pacemaker pulse vector will result in a recorded pacemaker pulse with a switched polarity. The recorded pacemaker pulse will then begin to increase as the angle between the precordial leads and the pacemaker pulse vector begin to align (albeit 180° out of phase).

This electrical characteristic is in stark contrast to the electrical characteristics of noise artifacts that are present in a recorded physiological signal. Most noise artifacts from external electromagnetic sources appear in the form of common mode noise. Since the source of the electromagnetic noise is at a relatively great distance, as opposed to the distance between the pacemaker pulse source or ECG signal source and the precordial electrodes, the noise generated by electromagnetic sources outside of the patient's body will generally effect all precordial electrodes in a similar fashion. Therefore, noise from electromagnetic sources outside of the patient will not exhibit such characteristics as the measured precordial sweep.

Referring back to FIG. 3, the measured precordial sweep determined in step 48 is used to adjust the pace pulse confidence interval in step 50. The determination of a presence of a precordial sweep by the pacemaker pulse may be used as an additional discriminator for characterizing an impulse in the ECG physiological signal as either a pacemaker pulse or a noise artifact. This additional information of the existence or non-existence of precordial sweep allows for the pace pulse confidence interval to be adjusted in step 50. Then, in step 52 the confidence intervals obtained for each impulse in the physiological ECG signal is then determined to be either a pacemaker pulse of a noise artifact based upon the confidence interval determined in step 50.

Finally, in step 54, an indication of the pacemaker pulses determined in step 52 is output to the monitoring or diagnostic system. The monitoring or diagnostic system 10 may use the pace pulse indication to denote the existence of the pace pulses on a display of the isolated and enhanced ECG signal. Alternatively, the diagnostic or monitoring system 10 may further store the pace pulse indications with the recorded ECG signal.

Figure 6:
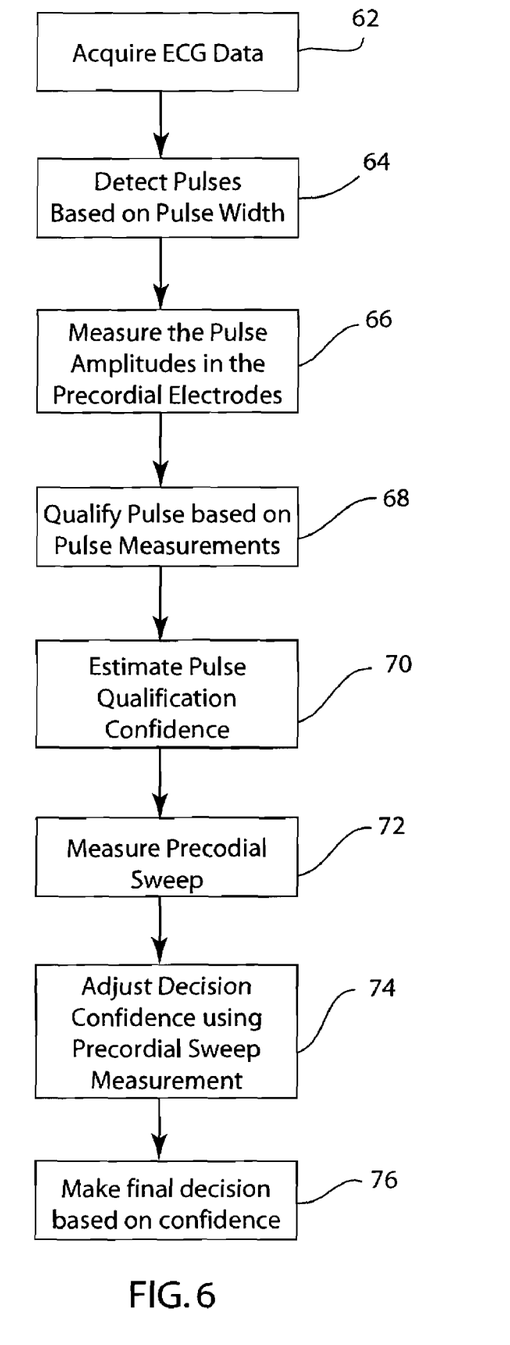
FIG. 6 is a flow chart of an embodiment of a method of identifying electronic therapeutic events from a physiological signal.

FIG. 6 is a flow chart depicting an alternative embodiment of a method for identifying pacemaker pulses. At step 62 ECG data is acquired from a patient. The ECG data may be acquired from the patient utilizing at least two precordial electrodes; however, it has been found that improved results may be obtained by the utilization of three or more precordial electrodes. Next, at step 64, impulses of interest, such as those that may be pacemaker pulses or noise artifacts, are detected based upon pulse width. An exemplary range of pulse widths that may be identified as impulses of interest may include those between 100 microseconds and two milliseconds. However, it is understood that this pulse width range may be broadened and/or narrowed depending on the characteristics of the signal being analyzed, the pacemaker pulse waveforms, noise artifact characteristics, or other signal processing considerations. Next, the amplitude of the impulses of interest are measured in step 66.

In step 68, the impulses of interest are qualified or examined based upon the pulse measurements taken in steps 64 and 66 to identify those pulses that are likely to be pacemaker pulses. Next, at step 70, a confidence interval is estimated for the pacemaker pulses qualified in step 68. The confidence interval determined in step 70 provides a first indication of those impulses likely to be pacemaker pulses.

Next, at step 72, the precordial sweep of the qualified impulses across the precordial leads is measured. This measurement of the precordial sweep identifies whether the impulse was generated internal or external to the patient's body and provides a discriminating factor between internally generated pacemaker pulses and externally generated noise artifacts.

The confidence interval for each likely pacemaker pulse as determined in step 70 is modified in step 74 to include the additional discriminating factor of the measured precordial sweep in step 72. Finally, a final decision as to whether an impulse is a pacemaker pulse or a noise artifact is made in step 76 based upon the confidence interval determined in step 74.

The method as herein disclosed may be implemented in a variety of ways, including implementation utilizing hardware, software, firmware, or a combination thereof. Additionally, a variety of decision making techniques may be utilized to implement specific steps as disclosed herein. Specific decision making techniques that may be implemented may include, but are not limited to: conditional logic, Bayesian discriminate functions, neural networks, support vector machines, linear discriminate functions, and decision trees. These and other techniques may be used alone or in combination to implement some or all of the steps as disclosed herein.

While ECG as been predominantly described in the present disclosure, the disclosure is not herein so limited. Embodiments of the systems and methods as disclosed herein may be implemented in conjunction of the monitoring of other physiological signals such as, but not limited to, electroencephalography (EEG), and electromyography (EMG). In implementation of the systems and methods as disclosed herein as applied to the monitoring of alternative physiological signals, the ECG pace pulse may be generically defined as any type of electronic therapeutic event generated internal to the patient. An electronic therapeutic event may be any of an electronic internal stimuli of the patient's body to effect a biopotential physiological signal such as an ECG, an EEG, or an EMG.

Further, as disclosed herein the term module has been used to indicate an implementation in hardware, software, or firmware that receives an input, performs a data processing function, and returns an output. Therefore modules implemented in hardware, software, or firmware may be interchangeable in a system and left to the discretion to the implementor based on considerations external to the implementation of the system and/or method as disclosed herein.

To the extent that embodiments as disclosed herein may be implemented solely via a computer, such implementations may provide the technical effect of improved detection of pacemaker, or other electronic therapeutic event, pulses and the identification of such within a recorded ECG, or other biopotential, signal. The improved identification of these therapeutic pulses or signals improves the ability of a system or device to identify the use of implanted electronic therapy, that otherwise may go unnoticed, or to reduce false positive identifications of electronic therapeutic events that did not occur.

This written description uses examples to disclose the invention, including the best mode, and also to enable any person skilled in the art to make and use the invention. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of identifying an electronic therapeutic event from a physiological signal obtained from a patient through a plurality of electrodes attached to the patient, the method comprising:

obtaining a plurality of physiological signals from the plurality of electrodes, the obtained physiological signals comprising biopotential data, therapeutic event data and noise;

removing the biopotential data from the physiological signals;

using a first technique to identify likely therapeutic event data;

comparing the identified likely therapeutic event data from each of the plurality of physiological signals; and refining the identification of likely therapeutic events based upon the comparison between each of the plurality of physiological signals.

2. The method of claim 1, wherein the step of comparing the identified likely therapeutic event data comprises comparing the therapeutic event data sweep across the plurality of physiological signals.

3. The method of claim 2, further comprising:

computing a confidence interval for each identified therapeutic event based on the results of the first technique;

modifying the confidence interval for each identified therapeutic event based on the results of the comparison between the therapeutic event data from each of the plurality of physiological signals.

4. The method of claim 3, wherein the first technique comprises measuring pulse width.

5. The method of claim 4, wherein the first technique comprises measuring pulse amplitudes.

6. The method of claim 3, wherein removing the biopotential data from the physiological data is performed using filtering.

7. The method of claim 3 wherein the biopotential data is an electrocardiograph and the therapeutic event data is a pacemaker pulse.

8. The method of claim 3, further comprising:
displaying the physiological data;
annotating the displayed physiological data to identify the occurrence of therapeutic events.

9. The method of claim 2 wherein the therapeutic event data sweep is based on the relation of the plurality of electrodes to the angle of a therapeutic event vector.

10. The method of claim 9 wherein comparing the therapeutic event data sweep includes the identification of opposite polarities of the therapeutic event data between leads with greater than 90° difference in angle from the therapeutic event vector.

11. A non-transitory computer readable medium configured with computer readable code, the computer readable medium being coupled to a processor, the execution of the computer readable code having the effect of:
receiving a plurality of physiological signals comprising at least one biopotential signal and at least one therapeutic event signal;
isolating the biopotential signals from the therapeutic event signals;
measuring signal characteristics of the therapeutic event signals to identify potential therapeutic events;
comparing the potential therapeutic events identified in each of the therapeutic event signals;
determining the validity of potential therapeutic events.

12. The non-transitory computer readable medium of claim 11 further configured such as to, upon execution, have the effect of:
computing a first qualification confidence interval based on the measured signal characteristics; and
computing a second qualification confidence interval based on the comparison of the potential therapeutic events;
wherein the validity of the therapeutic events is determined based upon the second qualification confidence interval.

13. The non-transitory computer readable medium of claim 12 wherein the potential therapeutic events from each physiological signal are compared to the potential therapeutic events from the other physiological signals and wherein the existence of a predetermined relationship between the therapeutic events of the plurality of physiological signals increases the confidence interval for the therapeutic events.

14. The non-transitory computer readable medium of claim 13 wherein the predetermined relationship between the therapeutic events is lead sweep.

* * * * *